United States Patent
Ritz et al.

(10) Patent No.: US 11,957,841 B2
(45) Date of Patent: Apr. 16, 2024

(54) RESUSCITATION AND VENTILATION MASK

(71) Applicant: International Health Group PTY LTD, Gordon (AU)

(72) Inventors: Gavin Herman Ritz, Gordon (AU); Deborah Jane Ritz, Gordon (AU)

(73) Assignee: INTERNATIONAL HEALTH GROUP PTY LTD, Gordon (AU)

( * ) Notice: Subject to any disclaimer, the term of this patent is extended or adjusted under 35 U.S.C. 154(b) by 353 days.

(21) Appl. No.: 16/624,862

(22) PCT Filed: Jun. 27, 2018

(86) PCT No.: PCT/AU2018/050653
§ 371 (c)(1),
(2) Date: Dec. 19, 2019

(87) PCT Pub. No.: WO2019/000036
PCT Pub. Date: Jan. 3, 2019

(65) Prior Publication Data
US 2020/0129718 A1    Apr. 30, 2020

(30) Foreign Application Priority Data

Jun. 27, 2017 (AU) ................. 2017204362

(51) Int. Cl.
*A61M 16/00* (2006.01)
*A61M 16/06* (2006.01)

(52) U.S. Cl.
CPC .... *A61M 16/0622* (2014.02); *A61M 16/0683* (2013.01); *A61M 2205/0216* (2013.01)

(58) Field of Classification Search
CPC .......... A61M 16/0622; A61M 16/0605; A61M 16/0611; A61M 16/0616; A61M 16/0666
See application file for complete search history.

(56) References Cited

U.S. PATENT DOCUMENTS

| 6,843,249 B2 * | 1/2005 | Bergamaschi | A61M 16/06 128/206.24 |
| 8,413,656 B2 * | 4/2013 | Warren | A61M 16/06 128/206.25 |

(Continued)

FOREIGN PATENT DOCUMENTS

| AU | 2016210611 A1 | 8/2016 |
| EP | 2954919 A1 | 12/2015 |
| WO | 2016/119006 A1 | 8/2016 |

OTHER PUBLICATIONS

Australian Patent Office/ISA, International Search Report and Written Opinion to PCT Application No. PCT/AU2018/050653, dated Aug. 27, 2018.

*Primary Examiner* — Michael R Reid
*Assistant Examiner* — Sarah B Lederer
(74) *Attorney, Agent, or Firm* — SoCal IP Law Group LLP; Angelo Gaz (57) ABSTRACT

A mask for the delivery of a medical gas under positive pressure. The engagement surface is generally circular in shape and is sufficiently rigid that operatively, when a suitable retention force is applied to the mask, an effective seal is produced at the interface of the engagement surface and the surrounding tissue primarily by deformation of the surrounding tissue.

17 Claims, 5 Drawing Sheets

(56) References Cited

U.S. PATENT DOCUMENTS

| | | | |
|---|---|---|---|
| 2015/0119742 A1* | 4/2015 | Tse | A61M 16/085 |
| | | | 128/200.26 |
| 2015/0335846 A1 | 11/2015 | Romagnoli et al. | |
| 2015/0352308 A1* | 12/2015 | Cullen | A61M 16/0875 |
| | | | 128/205.25 |
| 2016/0089261 A1 | 3/2016 | Quinn | |
| 2016/0279370 A1* | 9/2016 | McCracken | A61M 16/0616 |
| 2017/0049983 A1* | 2/2017 | Ellis | B29C 51/082 |
| 2017/0087321 A1* | 3/2017 | Jordan | A61M 16/06 |

\* cited by examiner

RESUSCITATION AND VENTILATION MASK

RELATED APPLICATION INFORMATION

This patent claims priority from International PCT Patent Application No. PCT/AU2018/050653, filed Jun. 27, 2018 entitled, "RESUSCITATION AND VENTILATION MASK", which claims priority to Australian Patent Application No. 2017204362, filed Jun. 27, 2017 all of which are incorporated herein by reference in their entirety.

TECHNICAL FIELD

The present invention relates to masks for delivering air or other gases to patients, particularly but not exclusively neonates.

BACKGROUND OF THE INVENTION

Masks are used in various clinical settings, such as hospitals, to deliver air, oxygen or other medical gases to patients. In some instances, they are a relatively loose fit and are not required to maintain a seal against the face.

However, in many instances it is desirable that a relatively tight fit is maintained. This is particularly the case where a gas is supplied under pressure to the patients, for example in a resuscitation situation, or to provide CPAP for a neonate.

For example, neonatal resuscitation typically takes place using a relatively sophisticated, controlled source of pressurised air and/or oxygen. This may include Positive End Expiratory Pressure and Peak Inspiratory Pressure (PEEP and PIP) to assist in correct lung inflation and improve blood oxygenation. It is understood in the art that it is critical to deliver air at the correct pressure, volume, gas mix and breathing rate, so that the neonate's lungs are not damaged, whilst an effective air flow to assist resuscitation is provided.

In order to achieve the desired outcome for the neonate, it is necessary that this air is effectively delivered through the mask in the desired way. If the mask is not relatively well sealed to the infant's mouth and nose, much of the air will leak out, and the desired delivery of air will not occur. This is a common situation in conventional practice.

The best practice for infant resuscitation is to hold the mask in the correct position on the face, whilst also supporting the neonate's head, and placing the neonate in the correct posture. This is a rather difficult task in practice, even with two practitioners assisting. It will be appreciated that the special needs and delicacy of a neonate necessitate the utmost care be taken in this procedure.

Co-pending application No. WO2016119006 by the present applicant discloses a mask for the delivery of medical gases, in which a peripheral sealing recess is provided, so that the recess can be connected to suction in order to retain the mask in position. Whilst this is very effective in practice, such an arrangement has not proved optimal for smaller premature neonates. It is also not suited to use for extended periods of time.

It is an object of the present invention to provide an improved mask for delivering medical gases to patients.

SUMMARY OF THE INVENTION

In a first broad form, the present invention provides a mask for delivering medical gases, wherein the engagement surface of the mask is more rigid than the tissue surrounding the airways with which it is engaged, so as to provide a seal by deforming the tissue which is engaged by the surface.

In another broad form, the present invention provides a collar for a mask, the collar being adapted to engage the outer surface of the mask and provide fixing points to allow the mask to be secured to the user, while spreading the forces associated with the mask fixation around the mask so that an effective seal between the mask and the skin of the user can be obtained.

According to one aspect, the present invention provides A mask for the delivery of a medical gas under positive pressure to a user, the mask including a body having an interior space, an engagement seal for surrounding the airway of a user and engaging surrounding tissue, the interior space being adapted in use to communicate with a source of medical gas and deliver the medical gas to the interior space, wherein the surface of the engagement seal is generally circular in shape and has a consistent cross-sectional shape which is substantially part circular, so that the surface of the engagement seal is substantially part toroidal, and wherein the engagement seal is sufficiently rigid that operatively, when a suitable retention force is applied to the mask, an effective seal is produced at the interface of the engagement seal and the tissue surrounding the airway of the user primarily by deformation of the tissue surrounding the airway, and without substantial deformation of the cross sectional shape of the of the engagement seal.

In one form, the mask further includes a removable collar, the collar being disposed around the mask, and including an annular flange extending around the mask, so that operatively when a downward force is applied to the collar during use, the force is distributed evenly around the engagement surface.

In another one form, the mask body is formed from a mask shell, the mask shell having a central opening surrounded by a peripheral recess adapted to receive suction, to thereby operatively affix the first mask shell to a user to facilitate the supply of a medical gas to a user, and an conversion insert, said insert on one side providing said engagement seal, and on the other providing a mating surface to engage the peripheral recess, so that the suction is no longer operative and the mask is solely retained and engaged by external retention pressure.

The general trend in mask design has been for an increasingly more flexible, compliant material and form to be used at the interface with the user, in an effort to optimise the seal which can be achieved. It has been determined by the inventor that contrary to this approach, a better seal can be obtained with a relatively less compliant material. The skin and underlying tissues on the face, particularly of neonates, are resilient and compliant. Using another soft, compliant surface does not optimise the seal—rather, a more rigid surface will maintain a good mechanical seal against the compliant skin and underlying tissue.

BRIEF DESCRIPTION OF THE DRAWINGS

Illustrative implementations of the present invention will be described with reference to the accompanying figures, in which.

Prior art

DETAILED DESCRIPTION OF THE INVENTION

The present invention will be described with reference to various specific implementations. It will be understood that the broad principles if the present invention can be implemented in a variety of structures and forms, and is not limited to the specific examples described.

The term 'medical gas' as used in the specification and claims is intended to be interpreted broadly. It encompasses air, oxygen, or a mixture thereof, either for resuscitation, CPAP, PEEP, PIP or any other purpose. It also encompasses other gases, for example for the delivery of different gas mixtures, therapeutic agents, anaesthetics, pharmaceuticals, or other agents, either alone or mixed with air. The gases may be either at ambient or another temperature. The gases may be delivered at a relatively low pressure, for example as supplementary oxygen, or at a higher pressure, for example for resuscitation. The gas may have particles or droplet entrained or mixed therein. The present invention is not limited in scope to any particular gas or treatment.

The term airway when used throughout the specification and claims refers to the mouth, the nose or both, as is appropriate for the particular application.

The main implementation to be described relates to a neonatal resuscitation system. However, the present invention may be applied to any situation where a medical gas is required to be delivered, and the mask is required to be correctly placed on the airways of a user. This includes, for example, resuscitation and ventilation systems, delivery of anaesthetics, delivery of gas carried treatments (for example for respiratory conditions), treatments for sleep disorders such as CPAP (continuous positive airway pressure) devices, and any other application where correct attachment of the mask around the airways may be useful.

The transition from foetal to extrauterine life is characterised by a series of unique physiological events. Among these, the lungs change from fluid-filled to air-filled, pulmonary blood flow increases dramatically, and intracardiac and extracardiac shunts initially reverse direction and subsequently close. Normal term newborns exert negative pressures as high as about −8.0 kPa when starting to expand their lungs.

For the first few breaths, these pressures are greater than those needed for subsequent breaths. Likewise, in those newborns that need assistance to initiate lung expansion, the fluid-filled alveoli may require higher peak inspiratory and end expiratory pressures than those commonly used in subsequent ventilation, or in resuscitation later in infancy.

There are significant differences in the respiratory systems of neonates, children and adults. Neonates are not small children and children are not small adults. The anatomy of an infant, head large, neck short, tongue large, narrow nasal passages which obstruct easily, larynx more cephalad (C4) and anterior, cricoid cartilage narrowest part of airway, epiglottis long and stiff, trachea short (~5 cm in newborns). The small radius of the trachea causes an increase in resistance to flow in the trachea; further, inflammation or secretions in the airway cause an exaggerated degree of obstruction in infants, and this is commonly found with neonates requiring resuscitation.

At birth the alveoli are thick walled and only number 10% of the adult total. Lung growth occurs by alveolar multiplication until 6-8 years. The airways remain relatively narrow until then. Ventilation is almost entirely diaphragmatic. Infant lungs have poor elastic properties. It takes some 2 years of life until the geometry of the rib cage changes, with the gradual development of the "bucket handle" configuration seen in the adult. Ribs tend to be more horizontal in infants and this limits the potential for thoracic expansion. (http://www.aic.cuhk.edu.hk/web8/Paediatric%20&%20physiology.htm)

Further, in terms of the biomechanics of ventilation, the chest wall compliance of infant is very high, and drops as they grow. In contrast, lung compliance is very low at birth and steadily increases through puberty. FRC of newborns are maintained through high respiratory rate, controlled expiration (laryngeal braking), and the tonic activity of ventilatory muscles.

The physiological dead space is approx. 30% of the tidal volume, as in adults, but the absolute volume is small, so that any increase caused by apparatus (mask or equipment) deadspace has a proportionally greater effect on infants. The problem is further exacerbated with premature neonates with their lungs (with significantly more problems) and body size being even smaller than full term newborns.

The newborn requiring resuscitation is very dependent on accurate delivery of air pressure and flow with almost no tolerance for variability of these factors. (Adult tolerances are significantly higher and they can survive with much higher variability). In other words the requirements for accuracy of ventilation are significantly more demanding for neonates than adults.

There have been very large increases in efficiency and effectiveness in neonatal resuscitation in recent years, with sophisticated resuscitation equipment producing very accurate delivery flows and pressures to the neonate. Resuscitation machines are used in labour and delivery wards, and neonatal Intensive care units (NICU) worldwide. Current neonatal resuscitation guidelines recommend the use of a T-piece device (part of the equipment delivery systems) with the potential of achieving controlled targeted Peak Inspiratory pressures (PIP) and delivering consistent Positive End Expiratory Pressure (PEEP) to help Functional Residual Capacity (FRC) and improve lung volume in the neonate. Target PEEP pressure are generally 0.5 kPa and PIP 2.5 kPa.

The T-piece connector in these systems connects onto special sized neonatal resuscitation masks. Air flows can range between 5 l/min and 15 l/μmin at specified pressures. T-piece circuits also typically include valves than can control the timing and flows of PEEP and PIP pressures.

Special sized and shaped masks have been designed and made to accompany neonatal resuscitation equipment. These masks are specifically designed to conform comfortably to an infant's face, facilitating an anatomical seal for the purposes of resuscitation and to meet all the other critical respiratory requirements mentioned above.

However these masks are required to fit the neonates face and make (ideally) 100% seals on the neonate's skin for the accurate delivery of PIP and PEEP pressures, no dead space and accurate flow rates. Due to the accurate pressures required mask leakage is the single biggest problem in neonatal resuscitation. In some studies, 14 to 80% leakage is found, even with experienced operators.

Conventional masks seek to provide a highly conformable, relatively soft and flexible engagement with the face of the user. For example, consider prior art FIG. 7. In this view, a cross sectional conceptual view of the mask 90 engaging with skin 97 is shown. This mask is of the type in which a balloon type seal is used, in which seal cushion 92 is highly flexible and filled with air 93. This structure is readily deformable, so that as a load is applied to mask 90, the seal spreads and bulges laterally. Because of the spreading horizontally, the area of the interface with the skin increase, and there is a low ability to load any section of the skin 97 vertically, and so the skin 97 and underlying tissue are only minimally deformed. Further, the seal cushion 92 is highly compressible and provides a poor interface with the skin 97, which like the seal is highly deformable. This can be seen at interface 96.

Figure 7:
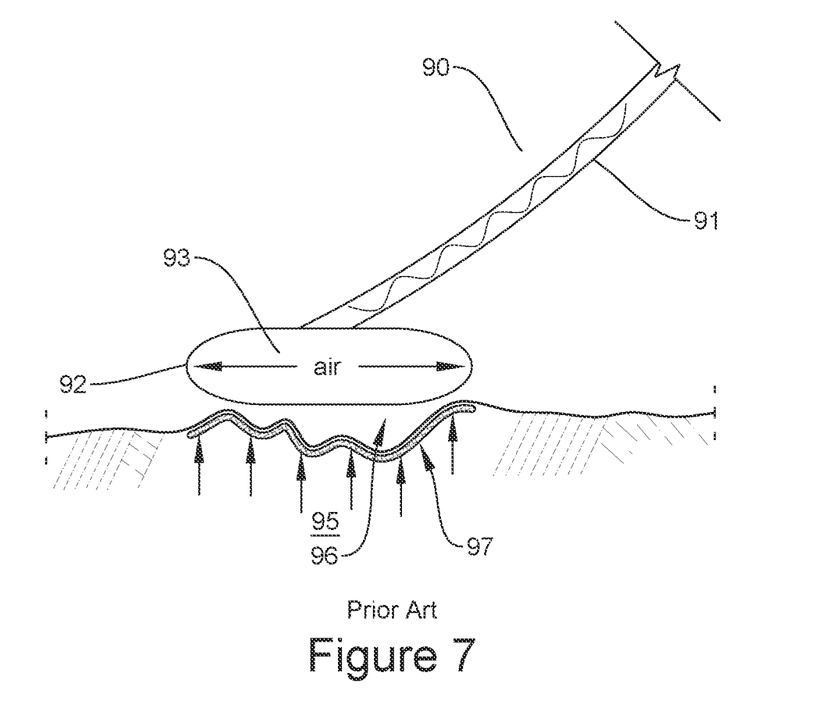
FIG. 7 illustrates the sealing operation of a prior art device.

Because the seal 92 compresses and deforms, it does not create an effective interface with the skin, and has a low interface connectivity with the skin. An air cushion as shown, or alternatively a well flexible and soft interface, are not able to provide a reliable seal, as by their nature they cannot be vertically loaded to any extent.

The inventors have identified that a more rigid while still sufficiently flexible device provides a superior seal in practice. Without wishing to be limited to this explanation, it is theorised that this is because the tissue around the airways, especially for neonates, and the soft, compliant mask structures are unable to exert a sufficient vertical (i.e. toward the body) force on each other to maintain a proper seal. By making the mask engagement less conformable, the tissue of the user performs the necessary small deformations relative to the mask to enable an effective seal to be made.

In a preferred form, the engagement surface is uniform in cross-section, and part circular in shape. The engagement surface is preferably toroidal, or strictly part toroidal, in shape. That is, the surface which provides an engagement with the tissue surrounding the airway is so shaped, and merges with the rest of the mask, which will have a different geometry. In an alternative implementation, the toroidal form could be a silicone gel, contained in a plastic skin which is less rigid but is sufficient to provide an effective seal according to the present invention. However, other cross-sectional shapes for the engagement surface are possible, but are preferably close to toroidal in form. The skilled reader will appreciate that small variations from this precise geometry are not consequential.

Figure 8A:
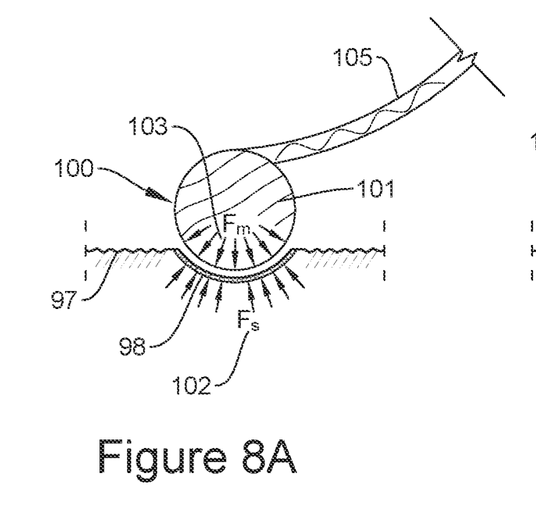
FIGS. 8A and 8B illustrate the sealing operation of implementations of the present invention.

FIG. 8A illustrates in a conceptual view of the interface between engagement seal 100 of mask 105 and skin 97. It can be seen that skin 97 is deformed with a part toroidal depression 98 corresponding to the shape of the surface of engagement seal 100. In a preferred form, the seal is formed from solid silicone with a shore A hardness of 5 to 25, or comparable material with an equivalent hardness.

The engagement seal 100 preferably depresses skin 97 along at least a third of the circumference of the seal 100, and remains in tight contact with the skin to provide an effective seal. $F_m$ 103 is the downward force of the engagement seal, and $F_s$ 102 is the upward reaction force of the skin and underlying tissue. For an effective seal, $F_m$ must more or less equal. In the absence of an effective $F_m$, for example it there is no infill material, or an air filled void, sealing force is no able to be effectively maintained at the interface. However, if $F_m$ is much greater than $F_s$, then this will be effective on softer tissue, but not on areas with minimal compliant underlying tissue, for example the nose.

Figure 8B:
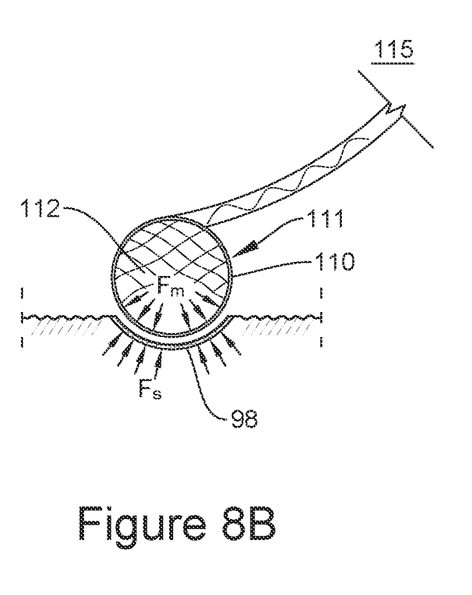

FIG. 8B is a similar illustration, but in which the mask 115 has an engagement seal 110 formed from a polymer skin 111 containing a silicone gel 112, having a shore A hardness of 5 to 25.

Thus, implementations of the present invention provide an effective seal primarily by a vertical load on the mask effecting deformation of the tissue surrounding the airway, and without substantial deformation of the engagement surface itself. It will be appreciated that the engagement surface will flex out of a flat plane along the central axis of the part toroidal structure, in order to mate with the skin of the user. However, there is no substantial deformation of the cross sectional shape of the engagement seal. Effective implementations require sufficient and necessary vertical loading and stiffness of the seal.

Implementations of the present invention have particular application to very preterm infants, for whom other mask sealing approaches, such as suction, are not suitable. However, the present invention is also more broadly applicable to any situation where medical gases are required to be delivered. It can be applied in hand held mode, or in an on-going application, as will be described further below.

The implementation of the present invention to be discussed below includes a mask structure (shape, material, flexibility, hardness) and mask function (gas flow, gas pressure, face adherence, suction pressure and flow) intended to conform to a pre-term newborn structure (anatomy of head, respiratory system) and newborn function (physiology of respiratory system).

It will be understood that the requirements for adult resuscitation and other uses are significantly different from the neonatal application discussed in detail. However, the general principle may be applied to other applications, for example in adults, with suitable modifications to structures, materials, dimensions and other characteristics.

Figure 1:
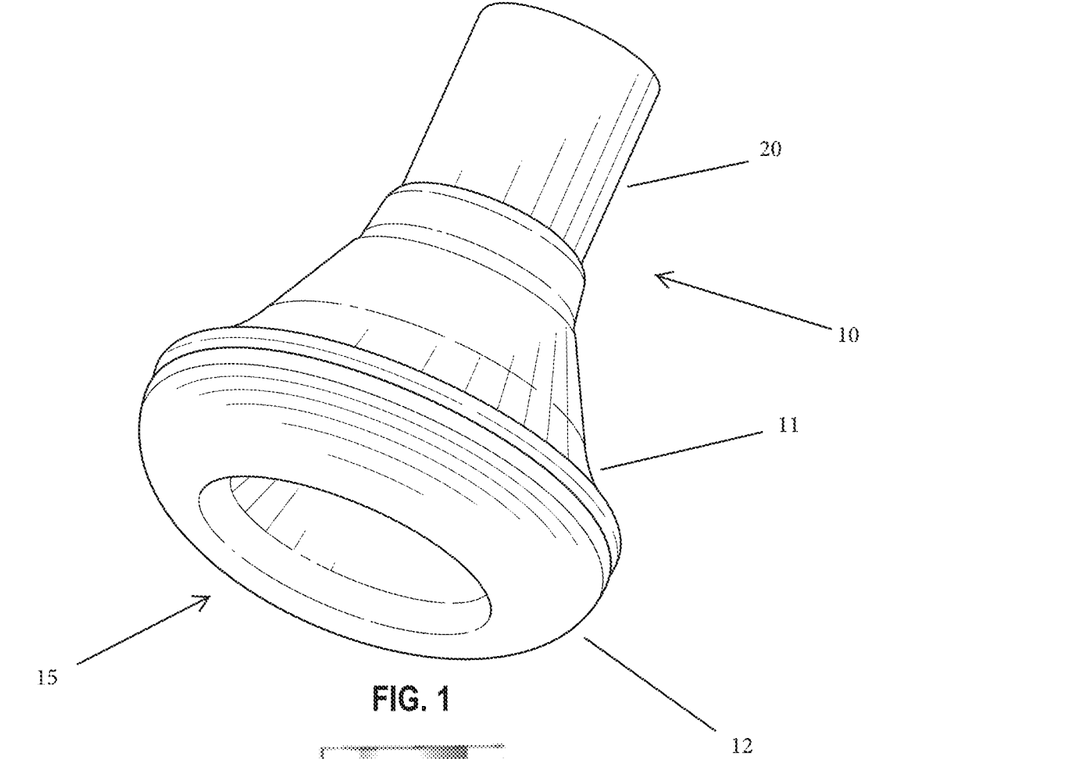
FIG. 1 is a perspective view of one implementation of the present invention.

FIG. 1 shows a mask 10 according to a first implementation of the present invention, with a neck section 20 for connection to a source of medical gas. It will be understood that appropriate connectors would be provided on the end of neck 20 in use.

Mask 10 has a generally part conical body section 11, connecting the neck 20 to the engagement 12. As can be seen, the outer and lower surfaces of engagement 12 are partly toroidal in shape, with an interior smooth bore 15. Bore 15 is the outlet for medical gas in use, while the engagement bears against the tissue surrounding the user's airway.

Figure 2:
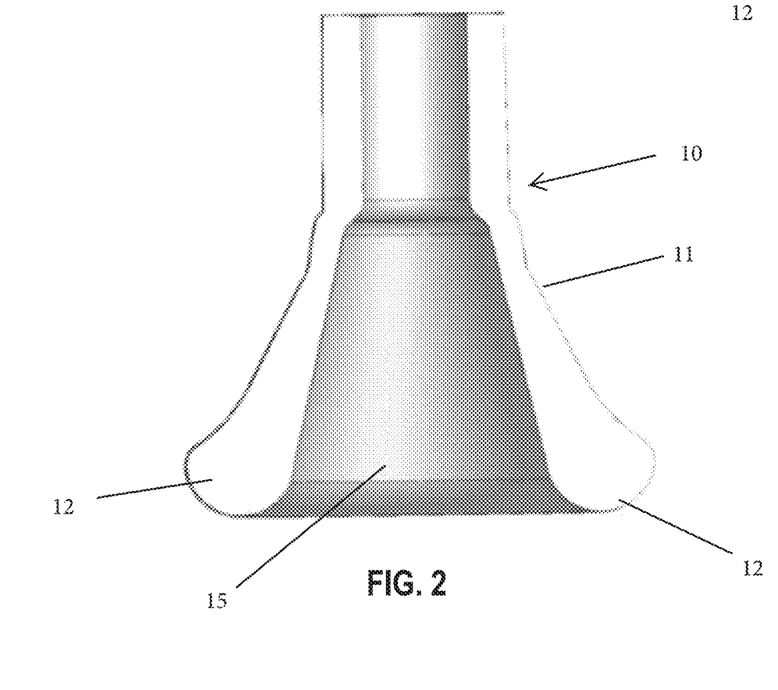
FIG. 2 is a cross-section view of the implement of FIG. 1.

FIG. 2 shows a cross section view of the mask 10 of FIG. 1. It can be seen that the body section is much thinner than the engagement section 12, and that internally the bore 15 provides an open passage for the delivery of medical gas.

Figure 3:
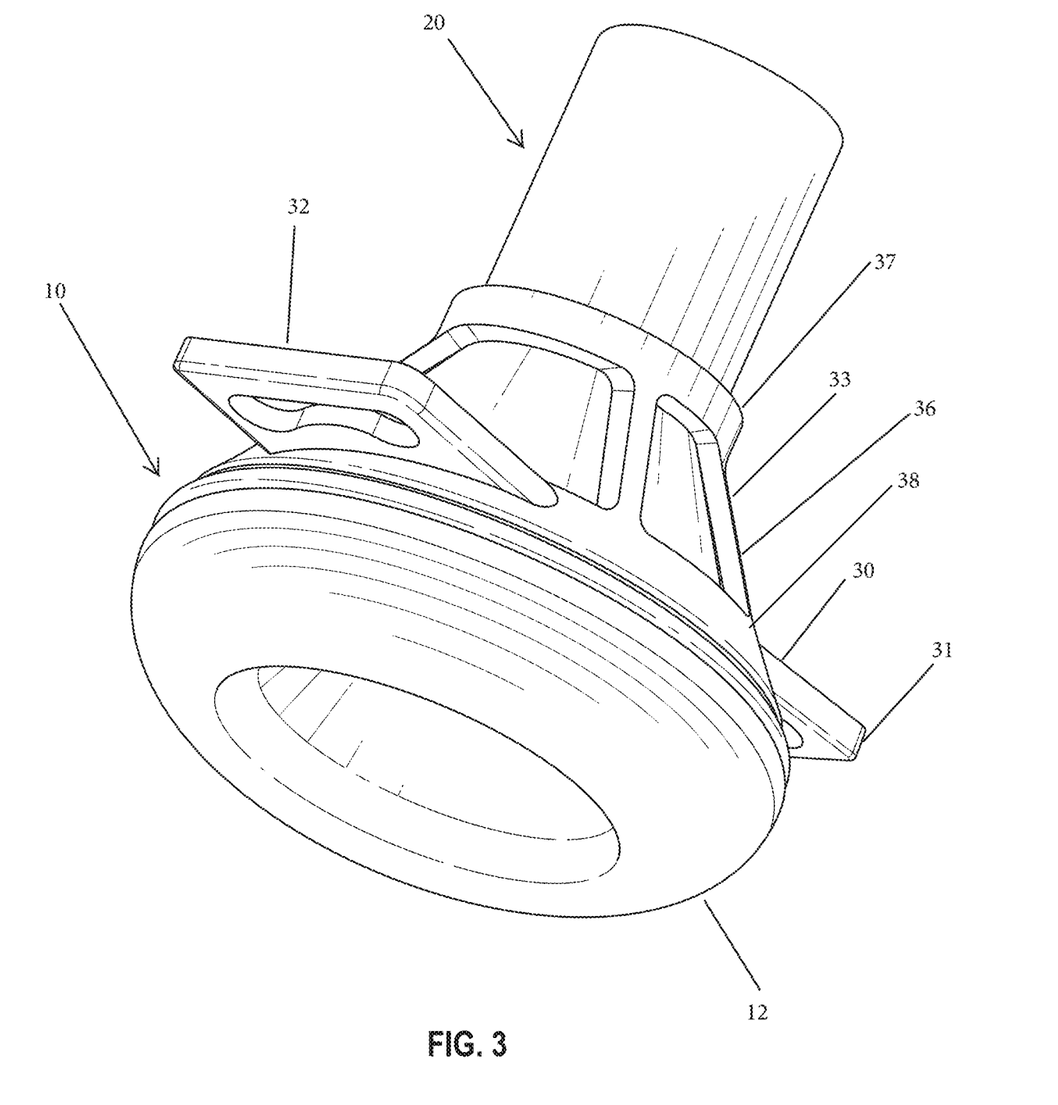
FIG. 3 is a perspective view of the implementation of FIG. 1, with an additional collar attached.

FIG. 3 shows the mask 10 with a collar 30 attached. One function of collar 30 is to provide a structure to which straps or other engagements can be attached, so as to fix the mask 10 into position on a user if required. Another function of collar 30 is to act as a loading device to spread the load associated with the straps evenly around the seal face. The T-piece 76 (see FIG. 6) fits snugly into the top of collar 30, and pressing down on T-piece 76 will provide a good seal between the mask 10 and the user, Collar 30 has a frame 33 to engage the exterior of the mask over a relatively wide area, so that forces from straps, etc., are spread around the mask's periphery, to provide a dispersed engagement. Frame 33 is formed from a ring 37, a flange 38, and connecting members 36. Ring 37 acts to retain the collar well centred around the neck section 20. Flange 38 extends around the exterior surface of the mask near to engagement section 12, and sits parallel thereto, so that it will evenly distribute forces from the collar to the engagement section 12 and maintain an effective seal in use.

Loops 31, 32 are provided to allow the attachment of straps. In this implementation, collar 30 is removable so that the mask may be used alone or with a collar. In other possible implementations, the collar could be integrated with the mask.

The mask is preferably moulded from a material such as silicone rubber. In an alternative implementation, a toroidal skin may be filled with a silicone gel. It is preferred that the material have a shore A hardness of about 5 to about 25. The purpose of the hardness range is to allow for the mask to conform to the anatomy of the user, without being so soft as to lose effective engagement with the skin.

The collet may be formed, for example by injection moulding, from any suitable polymer material, for example a bio-compatible injection moulded polymer. Because the mask is formed from silicone, it is not practical to provide attachments that are mechanically reliable for straps. Also, straps may be required, for example, in a CPAP application, but may not be needed or desired for a resuscitation situation. The separate collar allows for the practitioner to select the collar if needed. It may be used for any suitable mask, not only those according to the implementations discussed above.

The diameter of the mask will vary depending upon the age of the user. For a neonate, it typically will vary from 20 to 38 mm; for a full term infant, 50 mm. The circular shape means that there is no preferred orientation for the mask as it is place onto the user. It will be appreciated that the interior shape must provide enough clearance for the face and nose of the user.

The toroidal shape has been found to be very effective and to provide a better seal on an infant whose face is more or less round. The interior of the mask 10 is shaped so as to decrease dead air space. The external shape allows for the collar and/or fingers to concentrically apply pressure evenly to create a good seal between the mask 10 and the face.

It will be appreciated that providing an effective seal involves an interaction between the downward pressure applied, the shape and the hardness, as well as consideration of the anatomy which is to be engaged. The cross section of the torus in the preferred implementation does deform slightly in use. However, its interaction with the anatomy of the infant is still effective—the deformation does not extend to allow walls to collapse and cause air leaks. There is a symbiotic relationship between seal and anatomy, the skin pushes up and the seal pushes down at the "just right" hardness and conformity.

Whilst a very preterm neonate only has cartilage and not bone formation the hardness needs to be "just right" so as not to deform the cartilage of the pre-term. Downward pressure is required such that pressure does not deform the cartilage.

Figure 4:
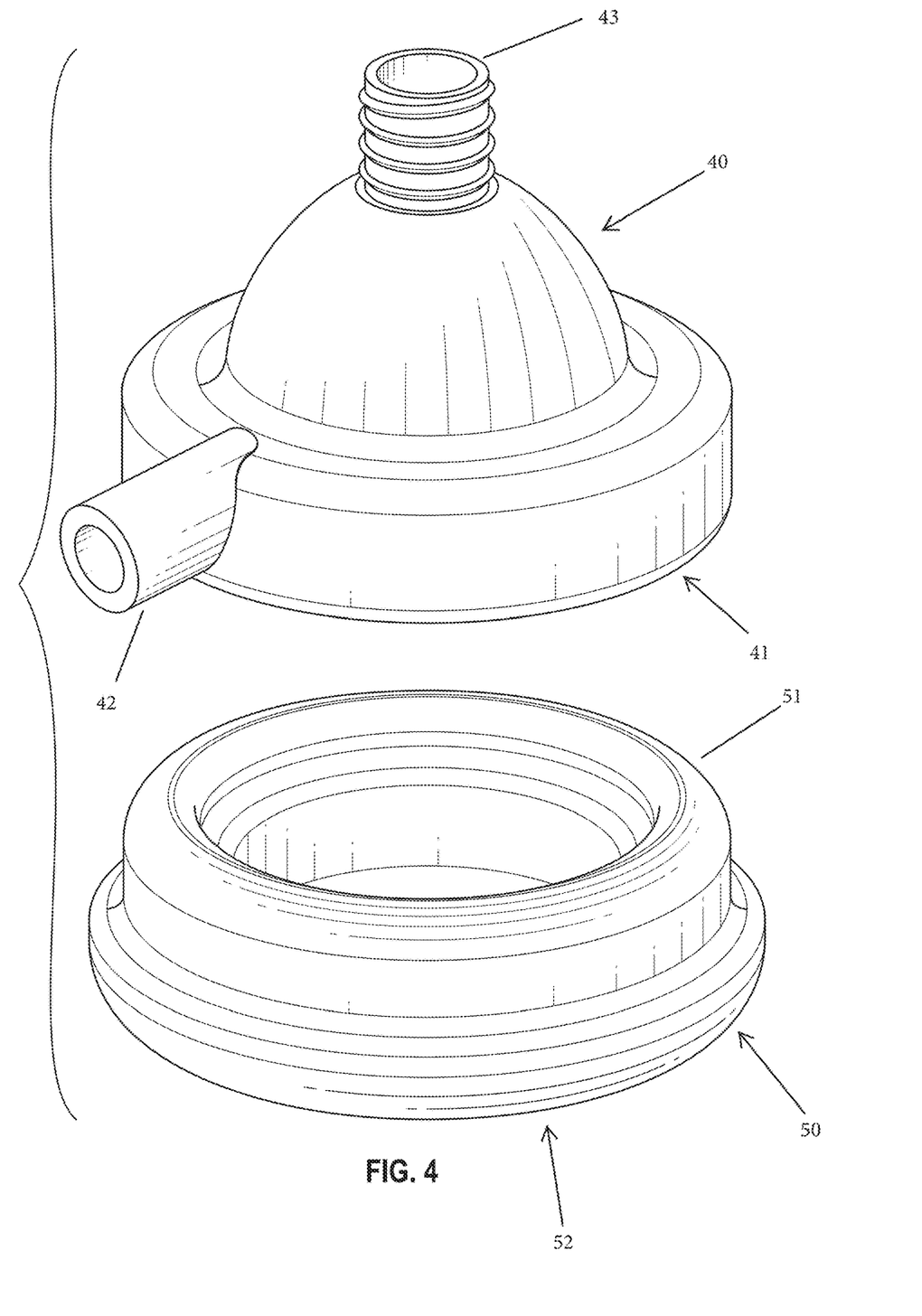
FIG. 4 is a perspective view illustrating an exploded view of a conversion device according to a second implementation.

FIG. 4 shows an implementation in which a mask which is adapted to be adhered by suction, for example as shown in the applicant's co-pending WO2016119006, can be modified by an insert to function according to the present invention. It will be appreciated that similar modification devices may be used with other types of mask if desired.

The prior art mask 40 has a connection 43 for a medical gas, a body 40, and an annular groove 41, connected to suction connection 42. In its original form, connection 43 is connected to a suitable medical gas supply, and connection 42 to suction. The annular groove is thereby at a reduced pressure, and pulls the mask 40 in to seal against a user's face.

However, it has been determined by the inventors that in some situations, this does not provide an effective seal. One particular example is for very early pre-term infants, for example 24 to 32 week neonates, where in some cases the skin is too soft for a good seal to be made. Another application is where on-going delivery of medical gases is required over a longer period, such as for infant or adult CPAP or delivery of anaesthetics.

Figure 5:
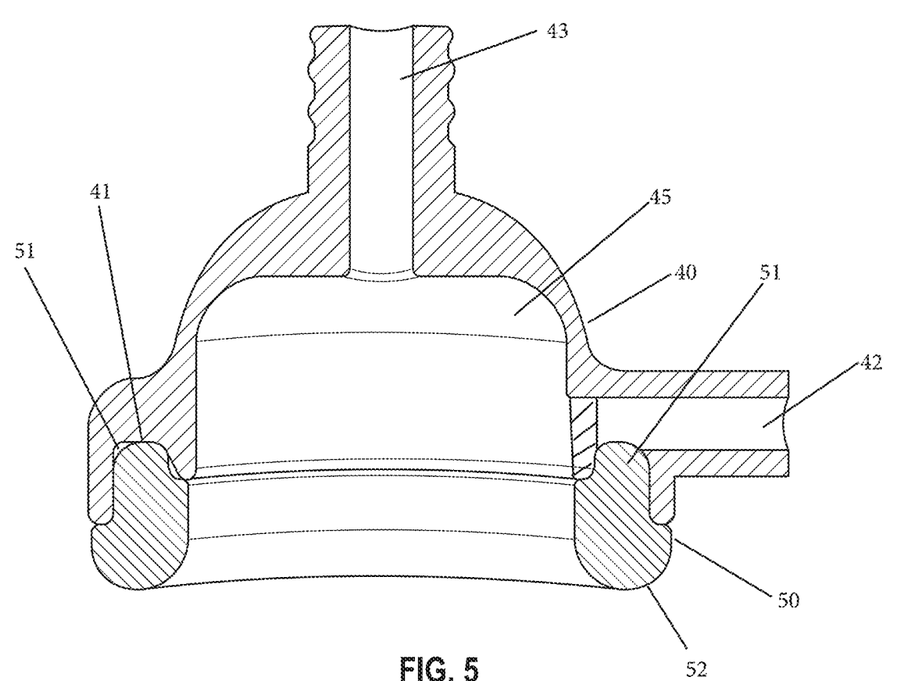
FIG. 5 is a cross-sectional view of the second implementation.

FIGS. 4 and 5 shows a converter insert 50 adapted to be inserted into mask 40 to convert it into a mask according to the present invention. Insert 50 has an upper projection 51 with a shape adapted to mate with the interior surface of annular groove 41. Upper projection 51 further blocks the connection between suction connections and the groove 41, so that this is not a path for the loss of pressure from the medical gas delivery.

The lower, engagement surface 52 is part-toroidal in form, and is made from a similar grade of silicone rubber to the first implementation. Thus, a similar seal and engagement can be produced to the first implementation, using a composite device.

In an alternative implementation, the toroidal form could be provided using a silicone gel with an toroidal tube.

An advantage of this implementation is that it provides the freedom for the practitioners to select the form of mask that they need. The converter insert can be quickly added if needed at the point of care. The medical staff are still using a familiar mask, but with a different attachment.

Figure 6:
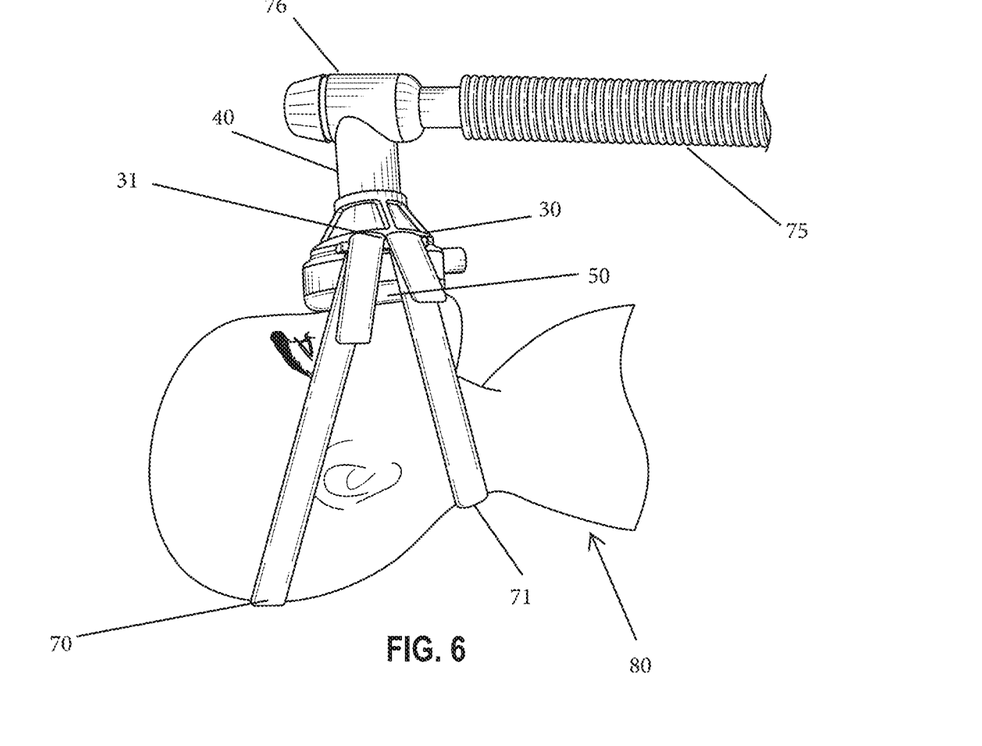
FIG. 6 is an illustration of one mode of use of the second implementation.

FIG. 6 shows an infant 80 with a mask 40 attached using collar 30. The mask has an attached insert 50, as in FIG. 5. Straps 70, 71 are attached to the collar 30 at loops 31, 32 (not visible) to retain the mask in engagement with the face of infant 80. Mask 40 is attached to a conventional T piece 76, and then to a source of medical gas via flexible pipe 75.

Masks according to the present invention may be applied by a practitioner in a conventional way, in a similar mode to existing masks.

The connections to medical gases are shown as conventional connections to neonatal resuscitation machines. It will be appreciated that different connections to the respective portions of the mask, which could be any suitable passage from the corresponding interior structure to the exterior connection or system, could be used. For example, the mask could be integral with the T piece device. The mask could be integrally connected to the appropriate pipes or hoses for connection to a suitable machine. No particular mode of connection is dictated in order to implement the present invention.

It will be appreciated that in a practical implementation, masks according to implementations of the present invention would be provided in a range of sizes, to suit full term and different sizes of pre-term neonates. Similarly, for children and adults, a range of sizes would be provided, so as to accommodate each specific individual.

In another implementation, where on-going use is contemplated, a custom sized device for a particular user could be made.

The disclosure of all patent, internet and other references cited above is hereby incorporated by reference into this description.

It will be appreciated that variations and additions are possible within the general inventive scope, and that all such variations and additions are encompassed with the present disclosure. All references to patent and other documents are hereby incorporated by reference into the description.

The invention claimed is:

1. A neonatal resuscitation mask for the delivery of a medical gas under positive pressure to a neonate, the mask including a body having an interior space, the body being generally frusto-conical and extending from a wider diameter adjacent a circular engagement seal to a narrower diameter at a distal end, a peripheral projection extending around the exterior of the body, the interior space being adapted in use to communicate with a source of medical gas at the distal end and deliver the medical gas to the interior space, the engagement seal being disposed directly below the peripheral projection, and being operatively adapted to surround the airway of the neonate and engage surrounding tissue, an interface of the engagement seal is configured to operatively seal with the tissue substantially outside the interior space, and wherein the engagement seal is solid and sufficiently rigid that operatively, when a suitable retention force is applied to the mask directly above the peripheral projection, an effective seal is produced at the interface of the engagement seal and the surrounding tissue primarily by deformation of the surrounding tissue.

2. A mask according to claim 1, wherein the mask and engagement seal operatively flexibly adapt to a general shape of the neonate's face, but the cross sectional shape of the seal does not deform substantially.

3. A mask according to claim 1, wherein the body of the mask is formed from a single material.

4. A mask according to claim 1, wherein the engagement seal is formed from a silicone rubber.

5. A mask according to claim 1, wherein the mask further includes a removable collar, the collar being disposed around the mask, and including a circular flange extending around the mask, so that operatively when a downward force is applied to the collar during use, the force is distributed evenly around the engagement surface.

6. A mask according to claim 5, wherein the collar further includes connections for attaching one or more straps, so that the mask may be held in place and a suitable retention pressure applied by said straps, so as to maintain an effective seal.

7. A mask according to claim 5, wherein the body of the mask is formed from a silicone rubber material, and the collar is formed from a more rigid polymer material.

8. A mask according to claim 1, wherein the peripheral projection is a ledge.

9. A neonatal resuscitation mask for the delivery of a medical gas under positive pressure to a neonate, the mask including a body having an interior space, the body being generally frusto-conical and extending from a wider diameter adjacent a circular engagement seal to a narrower diameter at a distal end, a peripheral projection extending around the exterior of the body, the interior space being adapted in use to communicate with a source of medical gas at the distal end and deliver the medical gas to the interior space, the engagement seal being disposed directly below the peripheral projection, and being operatively adapted to surround the airway of the neonate and engage surrounding tissue, an interface of the engagement seal is configured to operatively seal with the tissue substantially outside the interior space, and wherein the surface of the engagement seal has a consistent cross-sectional shape in the vertical direction which is substantially part circular, and the engagement seal is solid and sufficiently rigid that operatively, when a suitable retention force is applied to the mask directly above the peripheral projection, an effective seal is produced at the interface of the engagement seal and the surrounding tissue primarily by deformation of the surrounding tissue to have the consistent cross-sectional shape in the vertical direction which is substantially part circular.

10. A mask according to claim 9, wherein the mask and engagement seal operatively flexibly adapt to a general shape of the neonate's face, but the cross sectional shape of the seal does not deform substantially.

11. A mask according to claim 9, wherein the body of the mask is formed from a single material.

12. A mask according to claim 9, wherein the engagement seal is formed from a silicone rubber.

13. A mask according to claim 9, wherein the mask further includes a removable collar, the collar being disposed around the mask, and including a circular flange extending around the mask, so that operatively when a downward force is applied to the collar during use, the force is distributed evenly around the engagement surface.

14. A mask according to claim 13, wherein the collar further includes connections for attaching one or more straps, so that the mask may be held in place and a suitable retention pressure applied by said straps, so as to maintain an effective seal.

15. A mask according to claim 13, wherein the body of the mask is formed from a silicone rubber material, and the collar is formed from a more rigid polymer material.

16. A mask according to claim 9, wherein the peripheral projection is a ledge.

17. A mask according to claim 9, wherein in the vertical direction includes across the wider diameter.

* * * * *